United States Patent [19]

Hoiss

[11] Patent Number: 4,653,526
[45] Date of Patent: Mar. 31, 1987

[54] DIAPHRAGM VALVE

[76] Inventor: Jakob Hoiss, Ruffinistrasse 8/I, D-8000 Munich, Fed. Rep. of Germany

[21] Appl. No.: 825,862

[22] Filed: Feb. 4, 1986

[30] Foreign Application Priority Data

Mar. 2, 1985 [DE] Fed. Rep. of Germany ....... 3507412

[51] Int. Cl.$^4$ ............................ B08B 3/04; B08B 9/02; F16K 51/00
[52] U.S. Cl. .................................. 137/240; 73/863.86; 134/166 C; 137/241; 251/331
[58] Field of Search ........................ 73/863.84, 863.86; 137/238, 240, 241; 251/331; 134/166 C, 167 C, 168 C, 169 C

[56] References Cited

U.S. PATENT DOCUMENTS

| 2,936,998 | 5/1960 | Loepsinger | 251/331 |
| 2,981,660 | 4/1961 | Achorn, Jr. et al. | 137/240 |
| 4,051,865 | 10/1977 | Cocking et al. | 251/331 |
| 4,304,251 | 12/1981 | Schadel et al. | 137/240 |
| 4,344,453 | 8/1982 | Tuchenhagen et al. | 137/240 |
| 4,458,543 | 7/1984 | Mieth | 137/240 |

OTHER PUBLICATIONS

H. Bickel and K. H. Meyer, "Mikrobilogische Prüfung des Wassers im Rahmen der Inprozess-Kontrollen", pp. 285–290, Editio Cantor.

Primary Examiner—George L. Walton
Attorney, Agent, or Firm—Peter K. Kontler

[57] ABSTRACT

A diaphragm valve for removal of samples from a pipeline for water of predetermined microbiological purity has a body with a liquid-receiving inlet and an outlet which can be sealed from the inlet by the central portion of a substantially flat diaphragm. The outlet and that surface of the central portion of the diaphragm which overlies the intake of the outlet or which is adjacent to the intake of the outlet are sterilized with steam or with a liquid chemical which is admitted by a conduit at an acute angle to the direction of flow of samples through the outlet. Such sterilization takes place while the diaphragm seals the outlet and prior to removal of the first sample. The body of the valve can have a second outlet which is in continuous communication with the inlet. The liquid medium rinses and sterilizes the major part of the interior of the valve, irrespective of whether the inlet branches off a pipeline or is a part of the pipeline.

17 Claims, 4 Drawing Figures

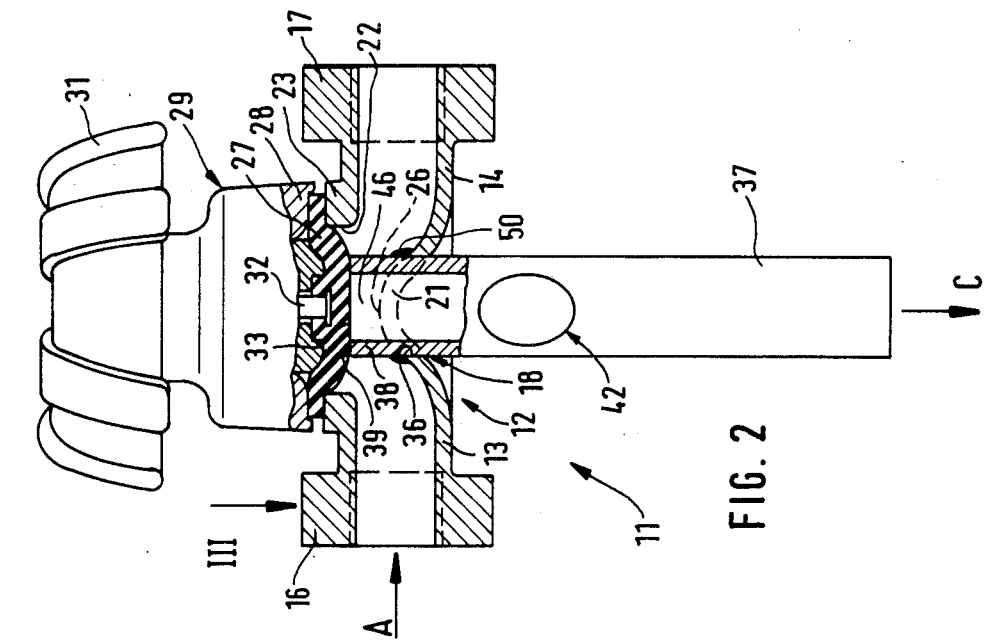
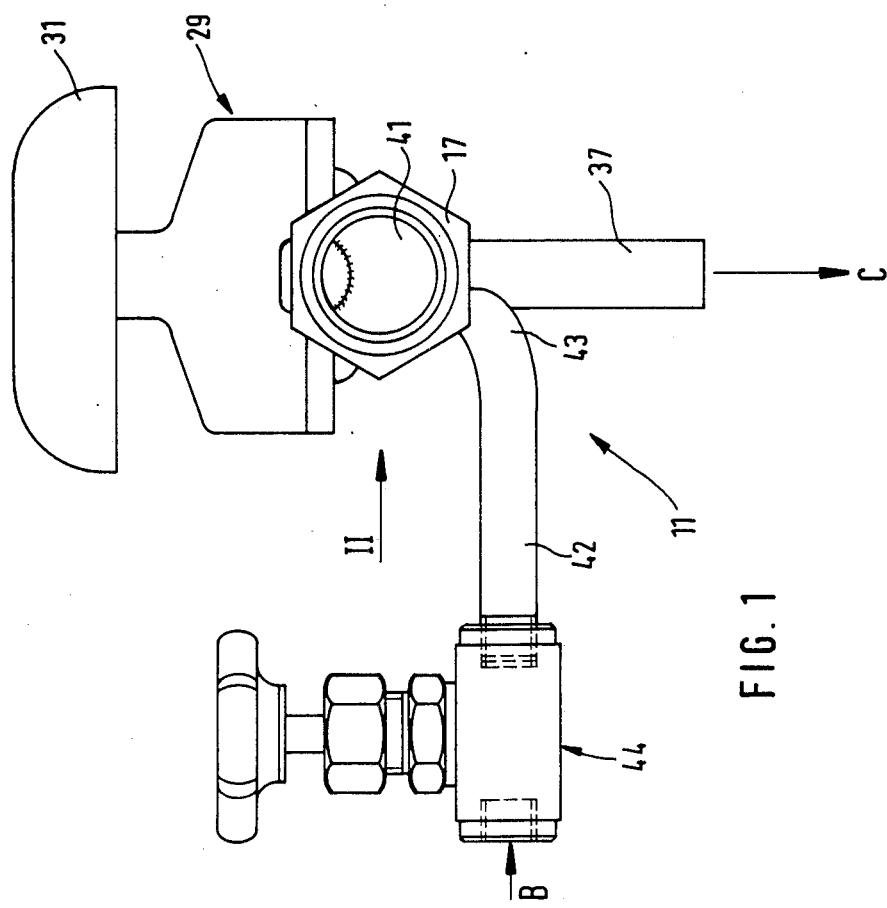
FIG. 2
FIG. 1

DIAPHRAGM VALVE

BACKGROUND OF THE INVENTION

The present invention relates to diaphragm valves in general, and more particularly to improvements in diaphragm valves for withdrawal of liquid samples from pipes. The diaphragm valve of the present invention can be utilized with advantage for removal of samples from pipes which contain a liquid (particularly water) of predetermined microbiological purity.

The article "Mikrobiologische Prüfung des Wassers im Rahmen der Inprozess-Kontrollen" by H. Bickel and K.-H. Meyer (published in "Die Pharmazeutische Industrie", Pharm. Ind. 42,1, pages 285–290, Editio Cantor, D-7960 Aulendorf, German Federal Republic) discloses a diaphragm valve which can be utilized for the above outlined purposes. When a nipple of the body of the valve which is disclosed in the aforementioned article is to receive a sample of the liquid medium, it must be subjected to flaming in order to ensure that the surfaces surrounding the path for the evacuation of samples are properly sterilized. This is a time-consuming operation and the application of heat is likely to result in damage to sealing elements including the diaphragm.

OBJECTS AND SUMMARY OF THE INVENTION

An object of the invention is to provide a novel and improved diaphragm valve which can be utilized for removal of liquid samples from pipelines or the like and which can be sterilized in an economical and time-saving manner.

Another object of the invention is to provide a diaphragm valve wherein certain components can be sterilized with readily available agents and whose elastomeric components need not be heated to an elevated temperature in the course of the sterilizing or disinfecting operation.

A further object of the invention is to provide a diaphragm valve which can be used as a superior substitute for heretofore known valves and which can be permanently or removably installed in or on a pipeline or the like.

An additional object of the invention is to provide a novel and improved method of sterilizing the above outlined valve.

A further object of the invention is to provide a novel and improved housing or body for use in the above outlined valve.

Another object of the invention is to provide a diaphragm valve which can be readily connected to available sources of sterilizing agents.

Still another object of the invention is to provide a diaphragm valve which can be properly manipulated by semiskilled or even unskilled persons and which can be operated manually or automatically.

An additional object of the invention is to provide a diaphragm valve wherein the extent and duration of the sterilizing operation can be selected at will.

The invention resides in the provision of a valve for removing samples from a liquid stream, particularly for removing samples of water exhibiting a given microbiological purity. The valve comprises a body which defines a chamber and has an inlet for admission of liquid into the chamber and at least one outlet for evacuation of liquid samples in a predetermined direction, a seat which is provided in the chamber, a valving element including a diaphragm having a portion (preferably its central portion) movable to and from an operative position of engagement with the seat in which the diaphragm seals the inlet from the outlet, means for moving the portion of the diaphragm to and from such position, a source of a suitable disinfecting agent (e.g., steam or a chemical solution), and means for admitting the disinfecting agent from the source into the outlet at an acute angle to the predetermined direction so that the admitted agent can enter a portion of the chamber and can contact a portion of the diaphragm on its way from the source into the chamber and thence into the outlet while the movable portion of the diaphragm is held in the operative position.

The one outlet can comprise a first elongated conduit and the admitting means can comprise a second elongated conduit which is arranged to admit the disinfecting agent into the first conduit in a second direction such that the inflowing agent has a component of flow counter to the predetermined direction.

The one outlet can constitute the sole outlet of the body, and such sole outlet can be aligned with the inlet. The body can include a protuberance which extends into the chamber, and the seat can be provided on such protuberance.

Alternatively, the body can be provided with the one outlet for removal of samples in the inoperative position of the movable portion of the diaphragm and with a second outlet which is preferably aligned with and is in permanent communication with the inlet by way of the chamber. The one outlet can include a conduit one end portion of which is disposed in the chamber and which can extend substantially at right angles to the inlet. The seat can be provided on the one end portion of the conduit. The body of the valve preferably includes a substantially undulate portion or protuberance which is disposed opposite the movable portion of the diaphragm. The conduit preferably extends into the chamber through such portion of the body. A welded seam or other suitable means can be provided to sealingly secure the one end portion of the conduit to the body. The one end portion of the conduit preferably extends into the chamber through and beyond the undulate portion of the body.

A marginal portion of the diaphragm, which surrounds the aforementioned movable portion, is preferably clamped or otherwise sealingly secured to the body of the valve.

The means for moving the movable portion of the diaphragm can comprise a handwheel or another manually movable element.

The novel features which are considered as characteristic of the invention are set forth in particular in the appended claims. The improved diaphragm valve itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is an elevational view of a diaphragm valve which embodies one form of the invention and wherein the valve body has two mutually inclined outlets;

FIG. 2 is a view as seen in the direction of arrow II in FIG. 1, the body of the valve and the diaphragm being shown in section;

DESCRIPTION OF THE PREFERRED EMBODIMENTS

Figure 3:
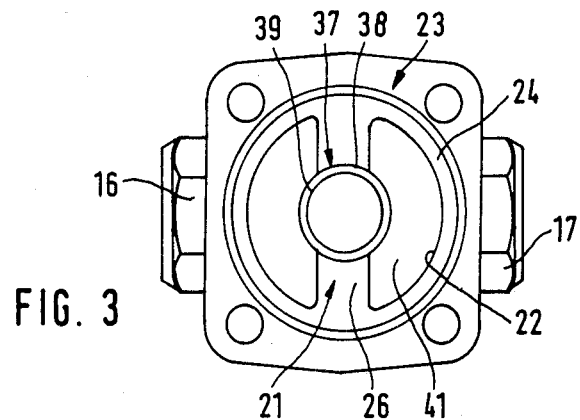
FIG. 3 is plan view of the body as seen in the direction of arrow III in FIG. 2.

FIGS. 1 to 3 show a diaphragm valve 11 which is used to remove liquid samples in response to movements of the central portion 33 of a substantially flat flexible diaphragm 27 from the operative or sealing position of FIG. 2. The liquid can be a stream of water having a predetermined microbiological purity and flowing from a source (not shown) in the direction of arrow A to enter an inlet 13 of the valve body 12 and to leave the internal chamber 41 of the body 12 by way of an outlet 14 which is in line with the inlet 13. The purpose of the valve 11 is to allow for thorough and reliable sterilization of the path for evacuation of samples of liquid which flows continuously or discontinuously in the direction of the arrow A, i.e., into the inlet 13, through the chamber 41 of the body 12 and out of the chamber 41 by way of the outlet 14. In accordance with a presently preferred embodiment of the invention, the valve 11 includes or is operatively connected with a source of steam (such source includes a normally closed manually operated shutoff valve 44 which can admit steam (or an aseptic liquid chemical sterilizing or disinfecting agent) in the direction of arrow B). Thorough sterilization of surfaces adjacent to the path for evacuation of samples of the liquid which flows from the inlet 13 toward and into the outlet 14 is desirable and advantageous because this prevents contamination of the samples during flow from the chamber 41 of the body 12 into a collecting receptable (not shown) or to another destination.

The inlet 13 has an internally threaded flange 16 which can receive the externally threaded discharge end of a first pipe (not shown) serving to admit a stream of liquid in the direction of arrow A, and the outlet 14 is connected with or includes an internally threaded flange 17 which can be connected to the externally threaded intake end of a second pipe (not shown) serving to convey the liquid to a selected destination. The internally threaded flanges 16, 17 can be replaced with slotted or otherwise apertured flanges which are attachable to the adjacent flanges of two pipes by means of bolts, screws or like fasteners. The flanges 16 and 17 can constitute separately produced parts which are welded or otherwise sealingly secured to the inlet 13 and outlet 14.

The central or median section 18 of the valve body 12 between the inlet 13 and the outlet 14 has an undulate portion in the form of a protuberance or barrier 21 which constitutes an extension of the lower portions of the inlet 13 and outlet 14 and extends into the chamber 41 opposite the mobile central portion 33 of the diaphragm 27. The section 18 of the body 12 is enlarged so that the stream of liquid which enters the chamber 41 via inlet 13 can flow around the central (highest) portion of the protuberance 21 and into the outlet 14 regardless of the position of the central portion 33 of the diaphragm 27. The central section 18 is further formed with an opening 22 which is disposed opposite the protuberance 21 and whose diameter is somewhat smaller than the diameter of the diaphragm 27. The marginal portion of the diaphragm 27 (i.e., that portion which surrounds the movable central portion 33) overlies a collar 23 which is an integral part of the section 18 and surrounds the opening 22. The marginal portion of the diaphragm is sealingly secured (clamped) to the collar 23 by a similar collar 28 on a housing 29 for a manually operable element 31 in the form of a handwheel serving to move the central portion 33 of the diaphragm 27 to and from the operative position of FIG. 2. The wheel 31 is mounted in the housing 29 in such a way that its axial position remains unchanged when it is rotated by the operator of the valve 11. Rotation of the wheel 31 entails axial movements of a spindle 32 which is non-rotatably but axially movably mounted in the housing 29 and whose lower end portion is secured to the central portion 33 of the diaphragm 27. The upper portion of the spindle 32 can be provided with an external thread in mesh with a nut (not shown) which is rotatable by the wheel 31. Other means for moving the central portion 33 of the diaphragm 27 can be used with equal advantage. For example, the valve 11 can be equipped with an electromagnetic, pneumatic, hydraulic or other device which can move the central portion 33 of the diaphragm 27 and can be actuated by remote control, e.g., from a control panel or the like.

The internal surface 24 of the collar 23 (i.e., that surface which surrounds the opening 22) is disposed at a level above the topmost part (upper side 26) of the protuberance 21 of the central section 18 of the valve body 12.

The central portion of the protuberance 21 is formed with a bore or hole 36 which is disposed opposite the central portion 33 of the diaphragm 27 and receives the upper end portion 38 of a second outlet in the form of an elongated conduit 37. The end portion 38 is sealingly secured to the protuberance 21 by a welded seam 50 and its upper end face defines or carries an annular seat 39 for the central portion 33. The liquid which enters the chamber 41 via inlet 13 is prevented from flowing into the outlet 37 when the spindle 32 maintains the central portion 33 of the diaphragm 27 in the operative or sealing position of FIG. 2. However, the diaphragm 27 cannot prevent the flow of liquid from the inlet 13 into the outlet 14 regardless of whether the central portion 33 is held in the position of FIG. 2 or in an inoperative position (i.e., at a level above and out of contact with the seat 39). The seat 39 is disposed at a level above the upper side 26 of the protuberance 21 but below the internal surface 24 of the collar 23 on the central section 18 of the valve body 12.

The means for admitting steam or another disinfecting agent into the chamber 41 (actually into the end portion 38 of the outlet 37 and against the underside of the central portion 33 of the diaphragm 27) includes a conduit 42 which receives the disinfecting agent from the source including the shutoff valve 44 and has an elbow 43 serving to discharge steam or a liquid sterilizing or disinfecting agent into the upper end portion 38 in such direction that the inflowing stream has a component of flow counter to the direction of flow (arrow C) of a sample from the chamber 41 through the outlet 37 and into a collecting receptacle or the like. The major part of the conduit 42 extends at right angles to the substantially vertical outlet 37. The shutoff valve 44 of the source of disinfecting or sterilizing agent can be opened by hand or by remote control, e.g., through the medium of an electromagnet (not shown) or the like.

The operation of the valve 11 is as follows:

When the liquid (e.g., water) is to flow solely from the inlet 13 into and from the outlet 14, the central portion 33 of the diaphragm 27 is held in the operative position of FIG. 2 so that the interior of the end portion 38 of the outlet 37 is sealed from the chamber 41. Thus, the entire liquid stream which enters the inlet 13 by flowing in the direction of arrow A is compelled to flow into the outlet 14 by flowing around the upper end portion 38 of the outlet 37. The aforementioned pipes which are connected to the flanges 16 and 17 can define an endless path for the circulation of microbiologically purified water. The manner in which the liquid entering at 13 can flow around the end portion 38 of the outlet 37 can be readily seen in FIG. 3 which shows that the diameter of the chamber 41 greatly exceeds the outer diameter of the end portion 38 and of the seat 39 thereon. The narrowest portion of the path for the flow of liquid from the inlet 13, around the end portion 38 and into the outlet 14 is shown at 46 (see FIG. 2). The liquid which flows through such narrowest portion or constriction 46 is free to contact the underside of the diaphragm 27 between the external surface of the end portion 38 and the internal surface 24 of the collar 23.

Prior to withdrawal of a sample via outlet 37, the internal surface of the outlet 37 and the underside of the central portion 33 of the diaphragm 27 (i.e., the underside of that portion of the diaphragm which is not contacted and rinsed by the liquid flowing from the inlet 13 toward and into the outlet 14) is sterilized by opening the valve 44 so that the latter admits a stream of steam or another disinfecting agent in the direction of arrow B. Such stream flows through the conduit 42 and enters the upper end portion 38 of the outlet 37 by way of the elbow 43 with the aforediscussed (upwardly directed) component of flow. This ensures reliable sterilization of the underside of the central portion 33 of the diaphragm 27. The sterilizing or disinfecting agent is evacuated by way of the outlet 37 in the direction of arrow C. A certain amount of sterilizing agent can flow from the elbow 43 directly into the lower portion of the outlet 37; such agent sterilizes only the internal surface of the outlet 37 at a level below the elbow 43. It will be seen that the sterilizing agent can contact all such surfaces of the diaphragm 27 and outlet 37 which are not rinsed (and thereby sterilized) by the stream of liquid entering the body 12 in the direction of arrow A and flowing through the inlet 13, through the chamber 41 and into and beyond the outlet 14.

In the next step, the person in charge opens or causes an opening of the valve 11 by manipulating the wheel 31 so as to lift the central portion 33 of the diaphragm 27 above and away from the seat 39 and thus establish a path for the flow of liquid from the inlet 13 and chamber 41 into the outlet 37. When the removal of a sample (e.g., a metered quantity of liquid which has entered at 13) is completed, the wheel 31 is actuated to return the central portion 33 to the operative position of FIG. 2 so that the liquid flows again only from the inlet 13 and toward, into and beyond the outlet 14.

The constriction 46 ensures that the liquid which flows from the inlet 13 is compelled or is at least highly likely to enter the outlet 37 as soon as the central portion 33 of the diaphragm 27 is lifted above and away from the seat 39 at the upper end of the inlet 37.

Figure 4:
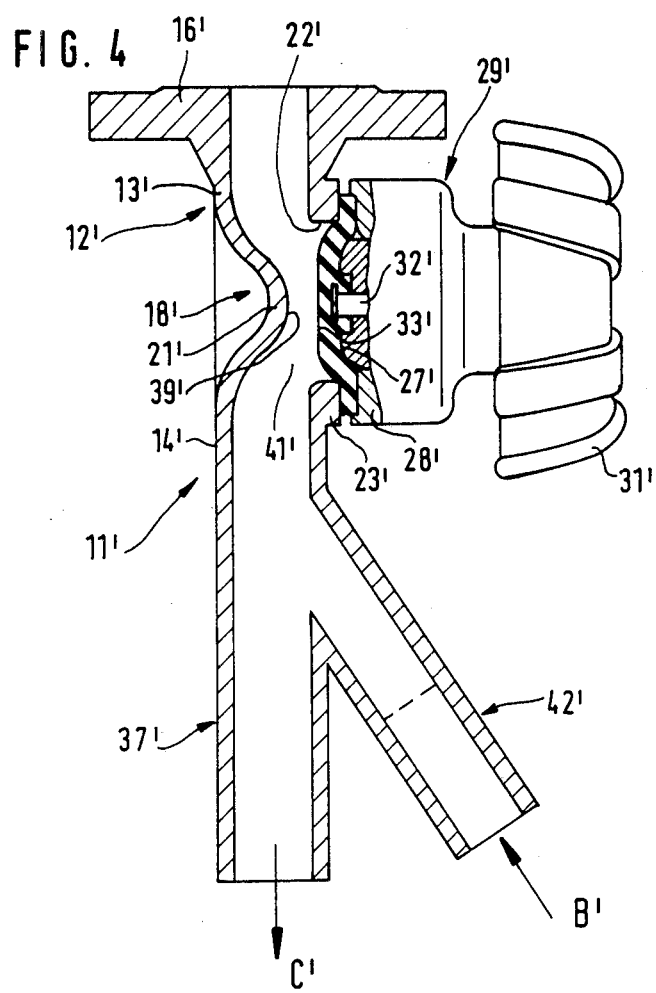
FIG. 4 is a partly elevational and partly sectional view of a modified valve wherein the body has a single outlet.

FIG. 4 shows a portion of a modified diaphragm valve 11' whose housing or body 12' is provided with a single outlet 37'. All such parts of this valve which are identical with or clearly analogous to the corresponding parts of the valve 11 are denoted by the same reference characters each of which is followed by a prime. The flange 16' of the inlet 13' is connected to the adjacent flange of a tee (not shown) which is provided in a pipe serving to convey the liquid (e.g., water having a predetermined microbiological purity) substantially horizontally as viewed in FIG. 4, i.e., substantially at right angles to the direction of liquid flow from the inlet 13' into and through the chamber 41' and thence into the single outlet 37' when the central portion 33' of the diaphragm 27' is held in the open or inoperative position of FIG. 4. The undulate portion or protuberance 21' of the central section 18' of the body 12' has a convex inner surface 39' which constitutes a seat and is normally engaged by the central portion 33' when the latter is held in the operative position. The means (including the spindle 32' in the housing 29' and the handwheel 31') for moving the central portion 33' of the diaphragm 27' to and from the operative position (in which the diaphragm seals the inlet 13' from the outlet 37') is or can be identical with the corresponding moving means of the valve 11. The movable portion 33' of the substantially flat diaphragm 27' is sufficiently large and sufficiently elastic to be capable of adequately engaging the seat 39' and of thereby sealing the inlet 13' from the outlet 37'.

The upper end portion 14' of the outlet 37' (as viewed in FIG. 4) is aligned with the inlet 13' and is integral with, or is separably connected to, a conduit 42' which can admit a jet or stream of steam or another disinfecting or sterilizing agent in the direction of arrow B' prior to removal of one or more liquid samples via outlet 37'. The stream of disinfecting agent flowing into the upper end portion 14' of the outlet 37' has a component of flow counter to the direction of flow of a sample from the inlet 13' into and beyond the outlet 37' (arrow C'). The shutoff valve of the source of disinfecting or sterilizing agent is not specifically shown in FIG. 4. The passages which are defined by the conduit 42' and the lower portion of the outlet 37' make an acute angle of approximately 30 degrees.

The operation of the valve 11' is as follows:

The flange 16' is attached to the flange of the aforementioned tee in the pipe for a liquid medium from which samples are to be removed in response to opening of the valve 11'. The inlet 13' is preferably short (i.e., the diaphragm 27' is preferably closely adjacent to the flange 16') so as to ensure that the liquid which flows in the pipe can continuously rinse the internal surfaces of the inlet 13' and its flange 16' as well as the upper part of the central portion 33' (the central portion 33' then engages the seat 39' so that the inlet 13' is sealed from the outlet 37'). The liquid which enters the inlet 13' while the valve 11' is closed returns into the pipe so that the inlet 13' and the upper part of the central portion 33' are continuously rinsed by fresh bodies of such liquid. Moreover, the inclination of inlet 13' with reference to the pipe causes at least some turbulence in the interior of the inlet 13' to thus further promote the rinsing action of the liquid.

If the operator wishes to remove one or more samples, the shutoff valve of the source of steam or the like is opened to admit steam into the chamber 41' whereby the steam contacts the lower part of the central portion 33' as well as the internal surface of the outlet 37' while the valve 11' remains closed. The uppermost portion 14' of the outlet 37' can be said to correspond to the upper end portion 38 of the outlet 37 of the valve 11 except that it does not have a seat for the diaphragm 27'. Spent steam leaves the valve 11' in the direction of arrow C'. When the sterilizing operation is completed, the operator closes the shutoff valve in the conduit 42' and manipulates the handwheel 31' in order to move the central portion 33' away from the seat 39' so that a metered quantity of liquid can flow from the inlet 13' into the outlet 37'.

An important advantage of the improved diaphragm valve is that the sterilizing operation can be carried out at temperatures which are highly unlikely to damage O-rings, other annular sealing elements, the diaphragm 27 or 27' and/or any other temperature-sensitive parts. This is due to the fact that the sterilizing operation need not involve flaming but merely involves contacting the outlet 37 or 37', certain portions of the diaphragm 27 or 27' and certain portions of the valve body 12 or 12' with steam or with a liquid or gaseous chemical. The afore-discussed inclination of a portion of or the entire conduit 42 or 42' relative to the direction (arrow C or C') of flow of a liquid sample through the outlet 37 or 37' ensures predictable and reliable sterilizing of that portion of the diaphragm 27 or 27' which is not contacted by the liquid medium when the valve 11 or 11' is closed, of that portion of the body 12' which is not contacted by the liquid medium when the valve 11' is closed, and of the internal surface of the outlet 37 or 37'. The sterilizing equipment is simple, compact and inexpensive because it includes the outlet 37 or 37' (such outlet defines the path for evacuation of spent disinfecting agent from the valve). As mentioned above, the temperature of steam is not sufficiently high to cause any damage to the diaphragm 27 or 27' and/or to any other temperature-sensitive parts of the valve 11 or 11' so that the sterilizing operation can be carried out by a semiskilled or unskilled person and its quality or effectiveness is not unduly affected even by a careless attendant. Prolonged exposure of a certain portion of the diaphragm 27 or 27' to the action of steam or a chemical sterilizing agent merely entails a more satisfactory sterilizing action but does not damage or otherwise undesirably affect the useful life and/or the sealing action of the diaphragm.

The valve 11' of FIG. 4 exhibits the advantage that the outlet 37' and the conduit 42' can constitute integral parts of the valve body 12'. However, proper rinsing of the internal surface of the inlet 13', of the upper portion of the diaphragm 27' (in closed position of the valve 11') and of the upper portion of the valve body 12' depends on the extent to which the liquid medium is agitated and circulated in the interior of the inlet 13'. Therefore, and as mentioned above, the inlet 13' is preferably short so that the diaphragm 27' can be placed close to the aforementioned tee. When the valve 11' is closed, the inlet 13' can be said to constitute a blind alley wherein a certain amount of the liquid medium could settle and dwell for undesirably long intervals of time. In other words, the liquid medium in the inlet 13' (while the valve 11' is closed) could confine a body of liquid which, under adverse and unforeseen circumstances, could constitute a breeding ground for the development of microbiological and/or chemical impurities or contaminants. In order to account for such eventualities, the operator may wish to allow a certain quantity of liquid medium to flow from the inlet 13', through the outlet 37' into the drain or to other waste receiving means upon opening of the valve 11' and prior to actual removal of a sample. In this manner, the operator ensures that the body of liquid which has filled the inlet 13' immediately prior to opening of the valve 11' does not form part of the sample.

The embodiment which is shown in FIGS. 1 to 3 is preferred at this time because it excludes the possibility of accumulation of a stagnant body of liquid medium in the valve 11 in the operative position of the central portion 33 of the diaphragm 27. This is due to the fact that the body 12 is formed with two outlets and the outlet 14 is in continuous communication with the inlet 13 so that the liquid which enters the body 12 at 16 cannot stagnate in the chamber 41 and/or elsewhere in the valve body 12 at any stage of use of the improved valve. The valve 11 is installed in the pipeline for the main stream of the liquid medium and its interior (save for a relatively small portion of the diaphragm 27 and for the interior of the outlet 37) is continuously contacted by the flowing liquid medium so that the major part of the valve does not require any sterilization preparatory to removal of samples. In other words, the major part of the interior of the valve 11 is sterilized by the liquid medium which flows in the direction of the arrow A. Consequently, removal of the first sample can begin immediately after opening of the valve 11 (i.e., none of the liquid medium must be discarded for fear that the foremost part of the liquid medium entering the outlet 37 could be contaminated). If a certain quantity of liquid medium is discarded prior to removal of the first sample, the quantity of discarded liquid medium can be kept to a minimum.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A valve for removing samples from a liquid stream, particularly for removing samples of water exhibiting a given microbiological purity, comprising a valve body defining a chamber and having an inlet for admission of liquid into said chamber and at least one outlet for evacuation of liquid samples in a predetermined direction; a seat provided in said chamber; a valving element including a diaphragm having a portion movable to and from an operative position of engagement with said seat in which said diaphragm seals said inlet from said outlet; means for moving said movable portion of said diaphragm; a source of disinfecting agent; and means for admitting such agent from said source into said outlet at an acute angle to said direction so that the agent can enter a portion of said chamber and to contact another portion of said diaphragm on its way from said source into said chamber portion and thence into said outlet in the operative position of said movable portion of said diaphragm to sterilize said another diaphragm portion and said chamber portion prior to the removal of samples; said admitting means opening directly into said outlet.

2. The valve of claim 1, wherein said outlet comprises a first elongated conduit and said admitting means comprises a second elongated conduit arranged to admit the disinfecting agent into said first conduit in a second direction such that the inflowing agent has a component of flow counter to said predetermined direction.

3. The valve of claim 1, wherein said one outlet is the sole outlet of said body.

4. The valve of claim 3, wherein said body includes a protuberance extending into said chamber, said seat being provided on said protuberance.

5. The valve of claim 1, wherein said body has said one outlet and a second outlet which is in continuous communication with said inlet by way of said chamber.

6. The valve of claim 5, wherein said one outlet includes a conduit having an end portion disposed in said chamber, said seat being provided on the end portion of said conduit.

7. The valve of claim 6, wherein said body includes a portion which is located opposite said movable portion of said diaphragm and said conduit extends into said chamber through said portion of said body.

8. The valve of claim 7, further comprising means for sealingly securing said end portion of said conduit to said portion of said body.

9. The valve of claim 7, wherein said portion of said body has an undulate shape.

10. The valve of claim 9, wherein the end portion of said conduit extends into said chamber through and beyond said undulate portion.

11. The valve of claim 1, wherein said diaphragm includes a peripheral portion surrounding said movable portion; and further comprising means for sealingly securing said peripheral portion to said body.

12. The valve of claim 1, wherein said moving means includes a manually movable element.

13. The valve of claim 1, wherein said inlet is aligned with said one outlet.

14. The valve of claim 1, wherein said outlet extends substantially at right angles to said inlet.

15. The valve of claim 1, wherein said body includes said one outlet and a second outlet which is aligned with said inlet, said inlet being in permanent communication with said second outlet by way of said chamber and said one outlet being inclined with reference to said inlet.

16. The valve of claim 1, wherein said diaphragm constitutes the sole valving element of said valve.

17. The valve of claim 16, wherein said seat constitutes the sole seat of said valve.

* * * * *